United States Patent
Chandramowli et al.

(10) Patent No.: US 11,433,012 B2
(45) Date of Patent: Sep. 6, 2022

(54) PEPTIDES FOR INCREASING MELANIN IN MELANOCYTES

(71) Applicant: Conopco, Inc., Englewood Cliffs, NJ (US)

(72) Inventors: Ganesh Chandramowli, Bangalore (IN); Ian Peter Stott, Wirral (GB); Sreenivasa Thimmaiah, Kadur (IN)

(73) Assignee: Conopco, Inc., Englewood Cliffs, NJ (US)

( * ) Notice: Subject to any disclaimer, the term of this patent is extended or adjusted under 35 U.S.C. 154(b) by 190 days.

(21) Appl. No.: 16/763,207

(22) PCT Filed: Oct. 22, 2018

(86) PCT No.: PCT/EP2018/078916
§ 371 (c)(1),
(2) Date: May 11, 2020

(87) PCT Pub. No.: WO2019/096546
PCT Pub. Date: May 23, 2019

(65) Prior Publication Data
US 2020/0281837 A1    Sep. 10, 2020

(30) Foreign Application Priority Data

Nov. 14, 2017 (EP) .................................... 17201585

(51) Int. Cl.
*A61K 8/64* (2006.01)
*A61Q 19/04* (2006.01)

(52) U.S. Cl.
CPC ............... *A61K 8/64* (2013.01); *A61Q 19/04* (2013.01)

(58) Field of Classification Search
None
See application file for complete search history.

(56) References Cited

U.S. PATENT DOCUMENTS

| | | | |
|---|---|---|---|
| 3,264,280 A | 8/1966 | Hofman Klaus et al. | |
| 4,683,244 A | 7/1987 | Moeller et al. | |
| 4,833,147 A | 5/1989 | Moeller et al. | |
| 8,338,364 B2 | 12/2012 | Hantash | |
| 10,093,698 B2 | 10/2018 | Chung et al. | |
| 2009/0053760 A1 | 2/2009 | Eggen et al. | |
| 2010/0104521 A1 | 4/2010 | Dal Farra et al. | |
| 2011/0312890 A1 | 12/2011 | Chandran | |
| 2012/0014885 A1* | 1/2012 | Collier | A61Q 9/00 424/59 |
| 2015/0152139 A1 | 6/2015 | Hantash | |
| 2015/0274776 A1 | 10/2015 | Peschard et al. | |

FOREIGN PATENT DOCUMENTS

| | | |
|---|---|---|
| EP | 1604647 | 12/2005 |
| JP | 10081607 | 3/1998 |
| WO | WO9617589 | 6/1996 |
| WO | WO9956740 | 11/1999 |
| WO | WO2004062607 | 7/2004 |
| WO | WO2005079744 | 9/2005 |
| WO | WO2005099664 | 10/2005 |
| WO | WO2007129270 | 11/2007 |
| WO | WO2012112851 | 8/2012 |
| WO | WO2013063615 | 5/2013 |

(Continued)

OTHER PUBLICATIONS

Brenner, et al.; The Protective Role of Melanin Against UV Damage in Human Skin ; Photochem Photobiol.; 2007; pp. 539-549; 84(3).
IPRP2 in PCTEP2018078916; Nov. 18, 2019.
Search Report and Written Opinion in PCTEP2018078916; dated Nov. 22, 2018; World Intellectual Property Org. (WIPO).
Search Report and Written Opinion in EP17201585; dated Feb. 6, 2018.
Yasunobu, K. et al.; Oxidation of Tyrosine-Containing; J. Biol. Chem.; 1959; 3291-3295; 234(12).
Schurink, M., et al.; Novel peptides with tyrosinase inhibitory activity; Peptides; 2007; pp. 485-495; 28(3).
Huang et al.,; Inhibition of the activity of mushroom tyrosinase by alkylbenzoic acids; Food Chemistry; 2006; pp. 1-6; XP25129660; vol. 94; Elsevier.

(Continued)

*Primary Examiner* — Jessica Worsham
(74) *Attorney, Agent, or Firm* — Stephanie S. DelPonte

(57) ABSTRACT

Disclosed is use of a compound of the formula (I) to increase the amount of melanin in melanocytes, where: R1 is formula (AA) in which, X is H, $CH_3$, $(CH_2)_n$—$CH_3$ or a substituted alkyl group, Y is H, $CH_3$, $(CH_2)_n$—$CH_3$ or a substituted alkyl group and Z is H or OH; and R2 is H, OH, $NH_2$ or —O—$(OH_2)_n\beta$ where, n=1 to 3 and $\beta$ is phenyl, naphthyl or alkyl group further optionally substituted with halogen, aryl or $NH_2$ group, where compound of formula 1 is not a compound in which X is H, Y is $CH_3$ and Z is OH.

1 Claim, No Drawings

(56) References Cited

FOREIGN PATENT DOCUMENTS

| WO | WO2014080376 | 5/2014 |
| WO | WO2015081306 | 6/2015 |
| WO | WO2015174599 | 11/2015 |

OTHER PUBLICATIONS

Search Report and Written Opinion in EP17205634; dated Feb. 5, 2018.
Search report and Written Opinion in PCTEP2018079973; dated Jan. 15, 2019.
Co-pending application, Filed on May 11, 2020, U.S. Appl. No. 16/763,208, Sreenivasa Thimmaiah et al.

* cited by examiner

PEPTIDES FOR INCREASING MELANIN IN MELANOCYTES

FIELD OF THE INVENTION

The invention relates to a method, a composition and use of certain peptides for modulating the colour of human skin, particularly to increase the amount of melanin in melanocytes which are present in our skin and hair.

BACKGROUND OF THE INVENTION

Some people are concerned with certain characteristics of their skin. For example, consumers with age spots or freckles often wish that such pigmented spots be less pronounced. Some others may wish to address darkening of skin caused by exposure to sunlight or alternatively may wish to lighten their natural skin color. These needs of consumers led to the development of products that reduce or delay the production of melanin in melanocytes (i.e. reduce melanogenesis).

On the other hand, there are people who desire darker skin tone or a tanned look.

The melanocytes transfer melanin to the keratinocyces which are in their vicinity where it (melanin) serves to protect cellular DNA from UV-induced damage by virtue of its ability to absorb UV-radiation. When the skin is exposed to UV light, the synthesis of melanin increases as does the transfer of melanin to the keratinocytes. This results in visible darkening of the skin color, which is known as a tan. Tanning due to over exposure to UV radiation is a known phenomenon. However, it is also known that such exposure to UV radiation causes accelerated aging which may lead to increased incidences of skin cancer.

Melanin is the black pigment present in our hair and skin and is synthesized by melanosomes from tyrosine. Melanosomes are organelles found in melanocytes, a cell type present at dermis-epidermis junction. Tyrosine is acted upon by an enzyme, tyrosinase, which is the key step in melanogenesis.

In the melanosomes, the melanin is synthesized from monomers and is transferred to the neighboring cells called keratinocytes. The keratinocytes divide and differentiate and thus transport the melanosome to the surface of the skin. The shade or hue of the colour of our skin depends on the number and the size of melanocytes, the melanin content and the rate of formation and migration/transfer of melanosomes to keratinocytes.

There are some peptides/peptidic derivatives known to affect pigmentation of skin. Particularly, tyrosine-containing peptides are known to be directly acted upon by Tyrosinase [Yasunobu et al. J. Biol. Chem. (1959) 234, #12, 3291-3295].

Tyrosine based Pentapeptide activators of Tyrosinase are known (US20150152139 A1, Escape Therapuetics Inc). One of the sequence entries therein is Tyrosine-Serine-X-Y-Z On the other hand, longer hexameric (U.S. Pat. No. 8,338,364 B2, Hantash Basil M, 2011) and octameric peptides (Schurink et al. Peptides 28 (3):485-495) have been reported as tyrosinase inhibitors.

US2015/0274776 AA (Sederma) discloses peptides containing the amino acid Proline.

SUMMARY OF THE INVENTION

In accordance with a first aspect is disclosed use of a compound of the formula (I) to increase the amount of melanin in melanocytes.

In accordance with a second aspect is disclosed a cosmetic composition comprising a compound of the formula (I).

In accordance with another aspect is disclosed a method of increasing the amount of melanin in melanocytes, comprising a step of applying thereto a compound of the formula (I).

In accordance with another aspect is disclosed use of a compound of the formula (I) in the manufacture of a composition for increasing the amount of melanin in melanocytes.

These and other aspects, features and advantages will become apparent to those of ordinary skill in the art from a reading of the following detailed description and the appended claims. For the avoidance of doubt, any feature of one aspect of the present invention may be utilised in any other aspect of the invention. The word "comprising" is intended to mean "including" but not necessarily "consisting of" or "composed of." In other words, the listed steps or options need not be exhaustive. It is noted that the examples given in the description below are intended to clarify the invention and are not intended to limit the invention to those examples per se. Similarly, all percentages are weight/weight percentages unless otherwise indicated. Except in the operating and comparative examples, or where otherwise explicitly indicated, all numbers in this description indicating amounts of material or conditions of reaction, physical properties of materials and/or use are to be understood as modified by the word "about".

Numerical ranges expressed in the format "from x to y" are understood to include x and y. When for a specific feature multiple preferred ranges are described in the format "from x to y", it is understood that all ranges combining the different end points are also contemplated.

As used herein the term "comprising" encompasses the terms "consisting essentially of" and "consisting of". Where the term "comprising" is used, the listed steps or options need not be exhaustive. Unless otherwise specified, numerical ranges expressed in the format "from x to y" are understood to include x and y. In specifying any range of values or amounts, any upper value or amount can be associated with any particular lower value or amount. Except in the examples and comparative experiments, or where otherwise explicitly indicated, all numbers are to be understood as modified by the word "about". All percentages and ratios contained herein are calculated by weight unless otherwise indicated. As used herein, the indefinite article "a" or "an" and its corresponding definite article "the" means at least one, or one or more, unless specified otherwise. The various features of the present invention referred to in individual sections above apply, as appropriate, to other sections mutatis mutandis. Consequently, features specified in one section may be combined with features specified in other sections as appropriate. Any section headings are added for convenience only, and are not intended to limit the disclosure in any way.

DETAILED DESCRIPTION OF THE INVENTION

Melanin is produced due to a complex set of reactions within the melanocytes involving, at a basic level, the enzyme tyrosinase and the aminoacid L-tyrosine. It is known that tyrosinase is an essential component of melanin synthesis. Tyrosinase catalyzes conversion of L-tyrosine to dopaquinone via L-DOPA (L-3,4-dihydroxyphenylalanine) as an intermediate. Dopaquinone undergoes further conversion to form melanin.

An increase in the amount of the biological pigment 'melanin' in the melanocytes is usually associated with cytotoxicity and uncontrolled proliferation. Some known agents are not as safe as they should be and examples include forskolin and IBMX (3-isobutyl-1-methylxanthine) Sunless tanning agents are formulated into two types of cosmetic products. Of these, the most traditional is the self-tanning lotion. The imparted benefit is to achieve a skin coloration equivalent to that achieved by from basking in the sun. More recently, a second product category has arrived. Therein a sunless tanning agent in small amounts is added to a typical moisturizing lotion.

Most prominent among the sunless tanning agents is dihydroxyacetone ("DHA" which chemically is 1,3-dihydroxy-2-propanone). DHA is believed to exert its effect through interactions between its hydroxyl groups and the amino groups of amino acids and peptides naturally occurring in the hydrolipid pellicle and first layers of the stratum corneum of the skin. These Maillard reactions are believed (see, e.g., Bobin et al., J. Soc. Cosmet. Chem. 35: 255 (1984)) to lead to formation of brown pigments in the skin, thereby giving it an appearance like that of a naturally obtained tan.

We have determined that some dipeptides are able to increase the amount of melanin in melanocytes. We have also observed under vitro conditions that some molecules, which can be represented by a Markush structure, increase the melanin in primary human melanocytes. It is believed that these materials act via cellular signaling route.

In one aspect the melanocytes are the melanocytes of human skin. Alternatively, the melanocytes are the melanocytes of human hair.

Further we have determined that the representative molecules of the Markush structure are efficacious at very low dosage and in this manner, they are different from the typical chemical dyes which directly undergo reactions to yield darker products. The efficacy of the selected molecules is comparable to known standards like IBMX and Forskolin but without the extent of cytotoxicity that is usually associated with IBMX and Forskolin.

Disclosed in accordance with the first aspect of the invention is use of a compound of the formula (I) to increase the amount of melanin in melanocytes,

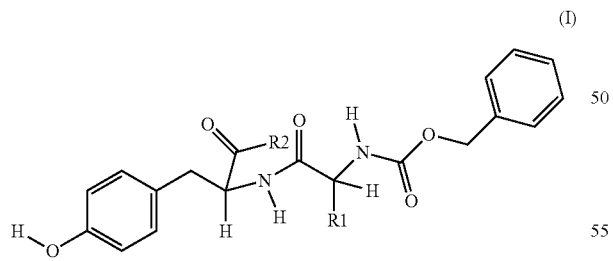

where:
R1 is

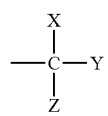

in which, X is H, $CH_3$, $(CH_2)_n$—$CH_3$ or a substituted alkyl group, Y is H, $CH_3$, $(CH_2)_n$—$CH_3$ or a substituted alkyl group and Z is H or OH; and R2 is H, OH, $NH_2$ or —O—$(CH_2)_n\beta$ where, n=1 to 3 and $\beta$ is phenyl, naphthyl or alkyl group further optionally substituted with halogen, aryl or $NH_2$ group; where compound of formula 1 is not a compound in which X is H, Y is $CH_3$ and Z is OH.

Particularly, it is preferred that when X is H, said Y is also H and said Z is OH. Alternatively, it is preferred that when said X is $CH_3$, said Y is also $CH_3$ and said Z is H.

Further, alternatively it is preferred that when said X is an alkyl or substituted alkyl group, said Y is H and said Z is H or OH.

It is preferred that in the compound of the formula (I), said X=Y=H, said Z=OH and said R2 is —O—$CH_2C_6H_5$. Further preferably in said compound of the formula (II), said X=Y=$CH_3$, said Z=H and said R2 is $NH_2$.

Particularly, it is preferred that the compound of the formula (I) is:

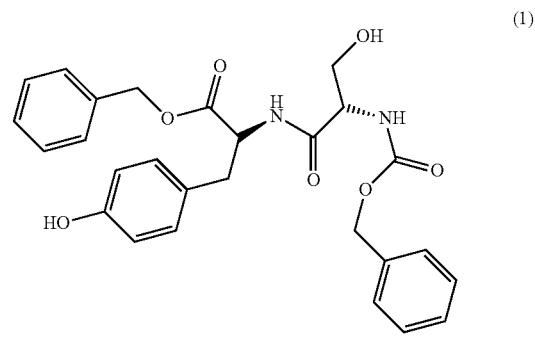

The name of this compound is Benzyl (2S)-2-[((2S)-2-{[(benzyloxy)carbonyl] amino}-3-hydroxypropanoyl) amino]-3-(4-hydroxyphenyl) propanoate, available Ex. SIGMA S786098.

Alternatively, the compound of the formula (I) is:

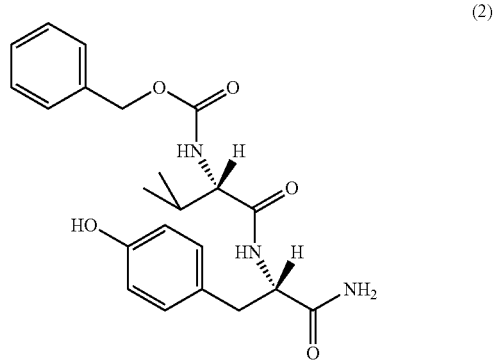 [SMILES: CC(C)[C@H](NC(=O)OCc1ccccc1)C(=O)N[C@@H](Cc1ccc(O)cc1)C(N)=O]

The name of this compound is Benzyl (1S)-1-({[(1S)-2-amino-1-(4-hydroxybenzyl)-2-oxoethyl] amino} carbonyl)-2-methylpropylcarbamate, available Ex. SIGMA S776688.

It has been observed the compounds of the formula (I) is effective at concentration of 1.5 to 50 µmoles under in vitro conditions. This observation indicates that the molecules are likely to efficacious at low dosage in compositions such cosmetic compositions, e.g., sunless tanning compositions.

It has been further observed that the use in accordance with this invention leads to an increase of 15 to 40% in the amount of melanin in the melanocytes as compared to its base (inherent) amount. It is a significant increase comparable to increase usually brought about by standard/known ingredients IBMX and Forskolin under identical test conditions. Usually the compounds or ingredients known for causing tanning/darkening of skin compounds have the propensity to alter/affect the enzymatic activity of tyrosinase. However, the use of a compound of the Formula (I), in accordance within the present invention does not alter/affect the enzymatic activity of tyrosinase. Therefore, the biological effect of the compound of the Formula (I), especially of the formulae 1 and 2, is likely via cellular signalling pathways.

Usually such compounds are associated with cytotoxicity which is an unavoidable side effect. However, it has been observed that preferably the cell viability of melanocytes with increased melanin is more than 75%, in more preferred cases more than 90% and in most preferred cases more than 95%. In other words, the cytotoxicity of the molecules of the formula (I) is less than 25%, preferably less than 10% and most preferably less than 5%. These numbers are under invitro conditions. It is preferred that the melanocytes are present in human skin or hair.

It is preferred that the use of a compound of the formula (I) is for non-therapeutic purpose. More preferably it is for cosmetic purposes. When it is for cosmetic purposes it is preferred that the concerned cosmetic composition is a sunless tanning composition, a moisturising lotion or a haircare product.

In accordance with another aspect is disclosed a method of increasing the amount of melanin in melanocytes comprising a step of applying thereto a compound of the formula (I).

A suitable skin surface includes facial skin, hands and arms, feet and legs and neck and chest. Of interest is facial skin including the forehead, perioral, chin, periorbital, nose, and/or cheeks. Further alternatively surface suitable for use in accordance with the present invention is human hair.

In accordance with yet another aspect is disclosed use of a compound of the formula (I) in the manufacture of a composition for increasing the amount of melanin in human skin.

In accordance with a further aspect is disclosed a cosmetic composition comprising a compound of the formula (I).

The composition may be applied and left on the desired surface for a sufficient time or may be applied repeatedly a sufficient number of times. In certain embodiments, the contact time is greater than about 1 hour, 2 hours, 6 hours, 8 hours, 12 hours, or 24 hours. The contact time is the time from application of the composition until the composition is removed. In certain embodiments, the composition may be removed by rinsing or washing the substrate. The composition may be removed by washing or rinsing the skin. The composition may be applied at least once daily. In other embodiments, the composition is applied at least twice daily. Multiple applications may occur over the course of at least about one week. Alternately, the application period may last more than about 4 weeks or more than about 8 weeks. In certain embodiments, the treatment period will extend over multiple months (i.e., 3 to 12 months) or years. In the case of cosmetic composition, the composition may be applied daily for prolonged period.

Compositions in Accordance with the Invention

In accordance with another aspect is disclosed a cosmetic composition comprising a compound of the formula (I),

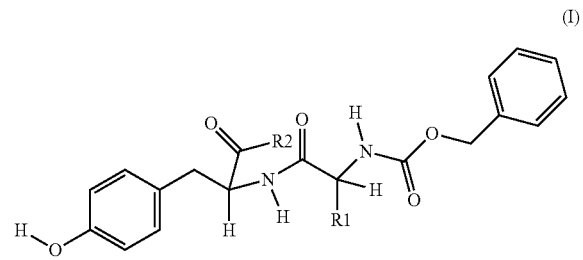

where:
R1 is

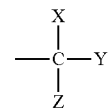

in which, X is H, $CH_3$, $(CH_2)_n$—$CH_3$ or a substituted alkyl group, Y is H, $CH_3$, $(CH_2)_n$—$CH_3$ or a substituted alkyl group and Z is H or OH; and R2 is H, OH, $NH_2$ or —O—$(CH_2)_n\beta$ where, n=1 to 3 and $\beta$ is phenyl, naphthyl or alkyl group further optionally substituted with halogen, aryl or $NH_2$ group; where compound of formula 1 is not a compound in which X is H, Y is $CH_3$ and Z is OH; and wherein the composition additionally comprises a cosmetically acceptable base selected from an aqueous base, an anhydrous base or an emulsion.

It is more preferred that the cosmetically acceptable base is an emulsion.

When the composition comprises an aqueous base, the aqueous base includes water. It may additionally include one or more of a surfactant, an emollient, a thickener or combinations thereof. When the composition comprises an anhydrous base, it may include an oil, a wax, an anhydrous solvent or mixtures thereof. When the composition comprises an emulsion, it includes both an oil phase and an aqueous phase and additionally an emulsifier to stabilize the emulsion.

It is preferred that the cosmetic composition is a skin care or skin cleansing composition. Alternatively, it is a hair care product. Examples thereof include hair oils, conditioners, hair colour and shampoos.

Preferably the cosmetic compositions in accordance with the invention comprise 0.05 to 10 wt % of the compound of the Formula (I).

The present inventors have found that the composition of the invention is capable of imparting tanning with use of compound of formula 1 with no additional contribution from use of dihydroxyacetone (DHA). DHA is a well known tanning agent which has been used for a long time. It is not necessary to boost the tanning efficacy of the composition of the present invention by including any DHA in it. Thus, it is preferred that the composition of the present invention comprises less than 1%, preferably less then 0.5%, further more preferably less than 0.1% DHA by weight of the composition; and optimally DHA is absent from the composition.

Other Ingredients

When the composition in accordance with the invention is cosmetic composition as above, it preferably comprises one or more of fragrance, surfactant, organic sunscreen, inorganic sunscreen, extender pigment and preservative.

Sunscreens include those materials which block harmful ultraviolet light. Preferred suncreens are the derivatives of p-aminobenzoic acid (PABA), cinnamate and salicylate. For example, avobenzophenone (Parsol® 1789), octyl methoxycinnamate and 2-hydroxy-4-methoxy benzophenone (also known as oxybenzone) can be used. Octyl methoxycinnamate and 2-hydroxy-4-methoxy benzophenone are commercially available under the trade marks, Parsol® MCX and Benzophenone-3, respectively. Ecamsule®, a benzylidene camphor derivative, and drometrizole trisiloxane, a benzotriazole, may also be used. Further examples include Octocrylene, phenylbenzimidazole sulfonic acid (also known as Ensulizole®), ethylhexyl salicylate, diethylhexyl naphthylate, bimotrizinole (trade marked as Tinosorb® S) and bisoctrizole (Tinosorb® M). Inorganic sunscreens include oxides like titanium dioxide and zinc oxide which reflect or scatter the sunrays. The quantity of sunscreens present in the compositions could vary depending upon the degree of protection desired from UV radiation. Preferably, the compositions comprise 0.01 to 15% by weight, more preferably 0.1 to 10 and most preferably 0.5 to 7.5% by weight sunscreen.

Illustrative examples of the types of fragrances that may be used include those comprising terpenes and terpene derivatives like those described in Bauer, K., et al., Common Fragrance and Flavor Materials, VCH Publishers (1990). Further examples include myrcene, dihydromyrenol, citral, tagetone, cis-geranic acid, citronellic acid, mixtures thereof.

The carrier acts as diluent or dispersant for the ingredients of the compositions. The carrier may be aqueous-based, anhydrous or an emulsion, whereby a water-in-oil or oil-in-water emulsion is generally preferred. If the use of water is desired, water typically makes up the balance of the composition, which most preferably is from 40 to 80% by weight of the composition.

In addition to water, organic solvents may optionally be included as carrier to assist any other carrier in the compositions of the present invention. Examples include alkanols like ethyl and isopropyl alcohol.

Other suitable organic solvents include ester oils like isopropyl myristate, cetyl myristate, 2-octyldodecyl myristate, avocado oil, almond oil, olive oil and neopentylglycol dicaprate. Typically, such ester oils assist in emulsifying the compositions, and an effective amount is often used to yield a stable, and most preferably, water-in-oil emulsion.

Emollients may also be used, if desired, as a carrier. Alcohols like 1-hexadecanol (i.e. cetyl alcohol) are preferred. Other emollients include silicone oils and synthetic esters. Silicone oils suitable for use include cyclic or linear polydimethylsiloxanes containing from 3 to 9, preferably from 4 to 5 silicon atoms. Non-volatile silicone oils useful as emollients include polyalkyl siloxanes, polyalkylaryl siloxanes and polyether siloxane copolymers. The non-volatile polyalkyl siloxanes useful polydimethylsiloxanes. Silicone elastomers may also be used. The ester emollients that may optionally be used are:

(i) alkenyl or alkyl esters of fatty acids having 10 to 20 carbon atoms. Examples thereof include isoarachidyl neopentanoate, isononyl isonanonoate, oleyl myristate, oleyl stearate, and oleyl oleate;

(ii) ether-esters such as fatty acid esters of ethoxylated fatty alcohols;

(iii) polyhydric alcohol esters. Ethylene glycol mono and di-fatty acid esters, diethylene glycol mono- and di-fatty acid esters, polyethylene glycol (200-6000) mono- and di-fatty acid esters, propylene glycol mono- and di-fatty acid esters, polypropylene glycol 2000 monooleate, polypropylene glycol 2000 monostearate, ethoxylated propylene glycol monostearate, glyceryl mono- and di-fatty acid esters, polyglycerol poly-fatty esters, ethoxylated glyceryl monostearate, 1,3-butylene glycol monostearate, 1,3-butylene glycol distearate, polyoxyethylene polyol fatty acid ester, sorbitan fatty acid esters, and polyoxyethylene sorbitan fatty acid esters are satisfactory polyhydric alcohol esters;

(iv) wax esters such as beeswax, spermaceti, stearyl stearate and arachidyl behenate; and, (v) sterols esters, of which cholesterol fatty acid esters are examples.

Emollients, when present, typically make up from 0.1 to 50% by weight of the composition, including all ranges subsumed therein.

Fatty acids having from 10 to 30 carbon atoms may also be included as carriers. Examples of such fatty acids include pelargonic, lauric, myristic, palmitic, stearic, isostearic, oleic, linoleic, arachidic, behenic or erucic acid and mixtures thereof.

Humectants of the polyhydric alcohol type may also be employed in the compositions. The humectant often aids in increasing the effectiveness of the emollient, reduces scaling at the skin surface, stimulates removal of built-up scale and improves skin feel. Typical polyhydric alcohols include glycerol, polyalkylene glycols and more preferably alkylene polyols and their derivatives, including propylene glycol, dipropylene glycol, polypropylene glycol, polyethylene glycol and derivatives thereof, sorbitol, hydroxypropyl sorbitol, hexylene glycol, 1,3-butylene glycol, 1,2,6-hexanetriol, ethoxylated glycerol, propoxylated glycerol and mixtures thereof. For best results, the humectant is preferably propylene glycol or sodium hyaluronate. Other humectants which may be used include hydroxyethyl urea. The amount of humectant may be 0.2 to 25% by weight and preferably from 0.5 to 15% by weight of the composition.

Moisturisation may be improved through use of petrolatum or paraffin. Thickeners may also be utilized as a portion of the carrier in the compositions. Typical thickeners include cross-linked acrylates (e.g. Carbopol® 982), hydrophobically-modified acrylates (e.g. Carbopol® 1382), cellulosic derivatives and natural gums. Among useful cellulosic derivatives are sodium carboxymethylcellulose, hydroxypropyl methylcellulose, hydroxypropyl cellulose, hydroxyethyl cellulose, ethyl cellulose and hydroxymethyl cellulose. Natural gums suitable for the present invention include guar, xanthan, sclerotium, carrageenan, pectin and combinations of these gums. Amounts of the thickener may range from 0.001 to 5, optimally from 0.01 to 0.5% by weight of the composition.

Surfactants may also be present. When present, the total amount of surfactants is 2 to 40% by weight, and preferably from 4 to 20% by weight, optimally from 5 to 12% by weight of the composition. The surfactant is selected from the group consisting of anionic, nonionic, cationic and amphoteric actives. Particularly preferred nonionic surfactants are those with a $C_{10-20}$ fatty alcohol or acid hydrophobe condensed with from 2 to 100 moles of ethylene oxide or propylene oxide per mole of hydrophobe; mono- and di-fatty acid esters of ethylene glycol; fatty acid monoglyceride;

sorbitan, mono- and di-C8-C20 fatty acids; block copolymers (ethylene oxide/propylene oxide); and polyoxyethylene sorbitan as well as combinations thereof. Alkyl polyglycosides and saccharide fatty amides (e.g. methyl gluconamides) are also suitable nonionic surfactants.

Preferred anionic surfactants include soap, alkyl ether sulfate and sulfonates, alkyl sulfates and sulfonates, alkylbenzene sulfonates, alkyl and dialkyl sulfosuccinates, $C_{8\ to\ 20}$ acyl isethionates, acyl glutamates, $C_{8\ to\ 20}$ alkyl ether phosphates and combinations thereof.

Various other ingredients may also be used in compositions. Actives are defined as skin benefit agents other than emollients and other than ingredients that merely improve the physical characteristics of the composition. Although not limited to this category, general examples include extender pigments such as talcs and silicas, as well as alpha-hydroxy acids, beta-hydroxy acids and zinc salts.

Beta-hydroxy acids include salicylic acid. Zinc oxide and zinc pyrithione are examples of useful zinc salts.

Compositions, especially those containing water, need to be protected against harmful microorganisms. Anti-microbial compounds, such as triclosan, and preservatives may become necessary. Suitable preservatives include alkyl esters of p-hydroxybenzoic acid, hydantoin derivatives, propionate salts, and a variety of quaternary ammonium compounds. Particularly preferred preservatives are methyl paraben, propyl paraben, phenoxyethanol and benzyl alcohol. Preservatives are from 0.1 to 2% by weight of the composition.

The packaging could be a patch, bottle, tube, roll-ball applicator, propellant driven aerosol device, squeeze container or lidded jar.

The invention will be explained in detail with the help of non-limiting examples.

EXAMPLES

Example 1: Increasing the Amount of Melanin in Melanocytes

All test compounds were purchased from SIGMA-ALDRICH as stocks of 10 mM in 100% DMSO. They were tested at various concentrations in cell culture (see below). Forskolin (SIGMA Cat. #F6886) and IBMX (SIGMA Cat. #I5879) were used as reference comparators, as they have been reported to increase melanin content. Neonatal foreskin primary human epidermal melanocytes were procured from Cascade Biologicals (labelled passage P0). Melanocytes were maintained in Medium 254CF (Cascade Cat. #M-254CF-500) supplemented with human melanocyte growth supplement (Cascade; Cat. #S-002-5), hereafter referred to as MGM. Cells were maintained at 37° C. in a humidified incubator with 5% $CO_2$ atmosphere.

Cell Viability and Melanin-Content Assay 50,000 cells were seeded in 24 well plate in MGM; after 24 hours, cultures were treated with various concentrations of the test materials and left undisturbed for a further period of 72 hours. Comparative vehicle controls of 0.25% (v/v) DMSO were also set up in parallel, simultaneously. At the end of the incubation period, cell viability was determined using the calcein method.

Briefly, cell culture spent media was removed and cells washed once with 0.4 ml of 1×PBS—Ca—Mg solution. Fresh 1 μM calcein-AM was added (0.2 ml/well), including to control wells without cells. Plates were covered with aluminium foil and incubated for 30 minutes. at 37° C. in the regular $CO_2$ incubator. Calcein fluorescence was then measured (λmax 490 nm and λmax 520 nm) in TECAN® M1000 Infinite series plate reader.

Melanin Content Assay

After calcein fluorescence readings were obtained, cells were drained and added fresh 125 μl of 1N NaOH (in 10% DMSO) per well. Cells were lysed by resuspension and incubation (60° C./1 hour). Then this lysate was transferred to a fresh 386-well plate and measured OD405 nm in a TECAN M1000 plate reader (estimate of relative melanin content).

Calculations

Calcein fluorescence values were ratio converted in 0 to 100 scale (% viability), with 100 representing the value of the 0.25% DMSO sample. % Melanin content was calculated as the ratio between $OD_{405nm}$ value of any sample to that of DMSO reference sample. Normalized melanin content value was then calculated as 100*(% Melanin Content)/(% Cellular viability).

The percentage Increase in melanin content was estimated as [(Normalized melanin content)−100]

The following four molecules were tested:

TABLE 1

According to the invention

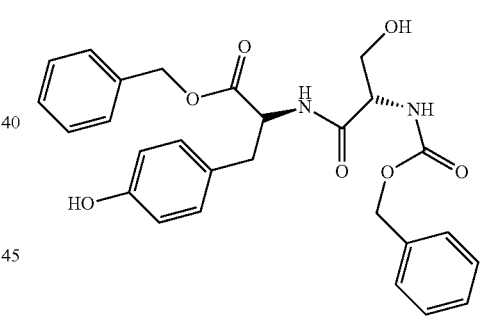

(Compound 1)

Benzyl (2S)-2-[((2S)-2-{[(benzyloxy)carbonyl]amino}-3-hydroxypropanoyl)amino]-3-(4-hydroxyphenyl)propanoate.

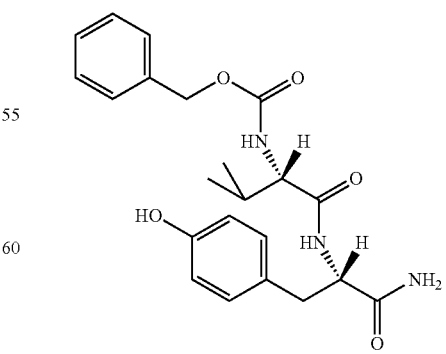

(Compound 2)

Benzyl (1S)-1-({[(1S)-2-amino-1-(4-hydroxybenzyl)-2-oxoethyl]amino}carbonyl)-2-methylpropylcarbamate

TABLE 1-continued

Outside the invention

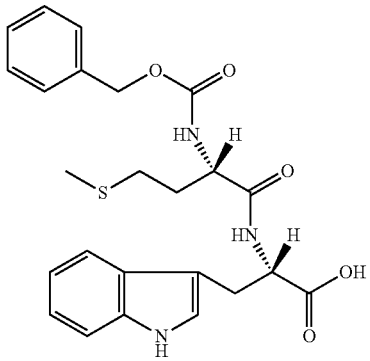 [SMILES: CSCC[C@H](NC(=O)OCc1ccccc1)C(=O)N[C@@H](Cc1c[nH]c2ccccc12)C(=O)O]

(Compound 3)

(2S)-2-{[(2S)-2-{[(benzyloxy)carbonyl]amino}-4-(methylthio)butanoyl]amino}-3-(1H-indol-3-yl)propanoic acid

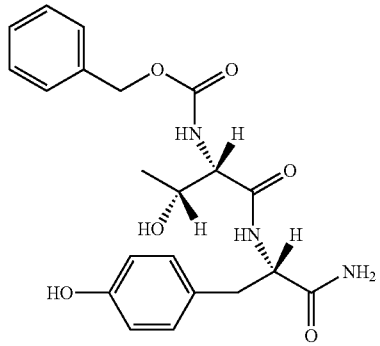 [SMILES: C[C@@H](O)[C@H](NC(=O)OCc1ccccc1)C(=O)N[C@@H](Cc1ccc(O)cc1)C(N)=O]

(Compound 4)

Benzyl (1S,2R)-1-({[(1S)-2-amino-1-(4-hydroxybenzyl)-2-oxoethyl]amino}carbonyl)-2-hydroxypropylcarbamate.

The data is summarised in Tables 2 and 3. All experiments were done at concentration of 0.25 µM. The control was DMSO (Dimethyl sulphoxide).

TABLE 2

| Compound | Calcein Fluorescence (arbitrary units) | % Viability | $OD_{405\,nm}$ | % Melanin | $100 * \dfrac{\%\ Melanin}{\%\ Viability}$ | % Increase in Melanin | % increase in Tyrosinase activity |
|---|---|---|---|---|---|---|---|
| Control | 100 | 100 | 0.113 | 100 | 100 | Nil | Nil |
| 1 | 107 | 107 | 0.153 | 135.4 | 126.5 | 26.5 | 3.5 |
| 2 | 81 | 81 | 0.125 | 110.6 | 136.5 | 36.5 | 2.0 |
| 3 | 99 | 99 | 0.120 | 106.2 | 107.3 | 7.3 | 1.8 |
| 4 | 110 | 110 | 0.116 | 102.7 | 93.4 | −6.6 | 0.8 |

The data in Tables 2 clearly indicates that compounds 1 and 2 (but not 3 or 4), lead to substantial increase in melanin content of melanocytes. When the compounds were tested separately in a Tyrosinase assay, none of them altered the enzymatic activity. Therefore, the biological effect of compounds 1 and 2 is likely via cellular signalling pathways.

Example 2: Dose Response

The observations are summarized in Table 3.

TABLE 3

| Material Tested @ % v/v | Calcein Fluorescence (arbitrary units) | % Viability | $OD_{405\,nm}$ | % Melanin | $100 * \dfrac{\%\ Melanin}{\%\ Viability}$ | % Increase in Melanin |
|---|---|---|---|---|---|---|
| 0.25 of control | 100 | 100 | 0.165 | 100 | 100.0 | Nil |
| 3.125 µM of 1 | 91.0 | 91.0 | 0.177 | 107.3 | 117.9 | 17.9 |
| 6.25 µM of 1 | 95.5 | 95.5 | 0.190 | 115.2 | 120.6 | 20.6 |
| 12.5 µM of 1 | 88.7 | 88.7 | 0.195 | 118.2 | 133.3 | 33.3 |
| 25 µM of 1 | 90.0 | 90.0 | 0.199 | 120.6 | 134.0 | 34.0 |
| 1.5 µM of 2 | 91.3 | 91.3 | 0.176 | 106.7 | 116.9 | 16.9 |
| 3.125 µM of 2 | 90.5 | 90.5 | 0.184 | 111.5 | 123.2 | 23.2 |
| 6.25 µM of 2 | 99.8 | 99.8 | 0.189 | 114.5 | 114.7 | 14.7 |
| 12.5 µM of 2 | 95.8 | 95.8 | 0.200 | 121.2 | 126.5 | 26.5 |
| 25 µM of 2 | 92.5 | 92.5 | 0.217 | 131.5 | 142.2 | 42.2 |
| 50 µM of 2 | 100.6 | 100.6 | 0.209 | 126.6 | 125.8 | 25.8 |
| 2.5 µM of Forskolin | 95.6 | 95.6 | 0.184 | 111.5 | 116.6 | 16.6 |
| 5 µM of Forskolin | 94.8 | 94.8 | 0.202 | 122.5 | 129.2 | 29.2 |
| 10 µM of Forskolin | 90.5 | 90.5 | 0.204 | 123.7 | 136.7 | 36.7 |
| 12.5 µM of IBMX | 100.1 | 100.1 | 0.193 | 116.7 | 116.6 | 16.6 |
| 25 µM of IBMX | 95.2 | 95.2 | 0.196 | 118.8 | 124.8 | 24.8 |
| 50 µM of IBMX | 91.0 | 91.0 | 0.193 | 116.7 | 128.2 | 28.2 |

The data in Table 3 indicates that the extent of increase in melanin content by compounds 1 and 2 is comparable to known standard reference molecules (Forskolin and IBMX). Also, the effect is observed with comparatively significantly lesser amounts of compounds 1 and 2. It rules out any potential oxidation of the Tyrosine phenolic side chain in those compounds resulting in increased $OD_{405nm}$.

The invention claimed is:

1. A method of increasing the amount of melanin in melanocytes comprising a step of applying a composition comprising compound

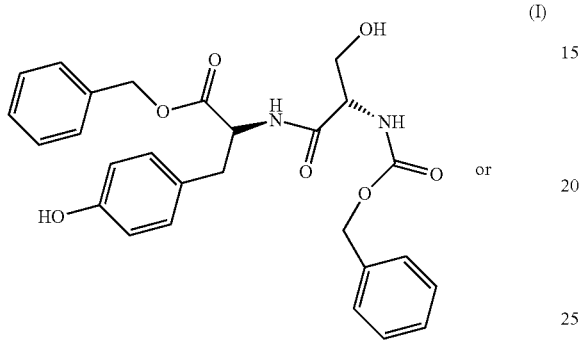
(I)

or

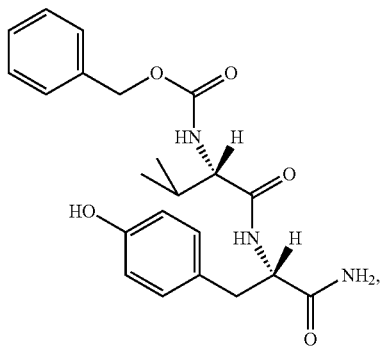
(2)

to human skin or human hair,
    wherein the composition additionally comprises a cosmetically acceptable base, and wherein the cosmetically acceptable base is an emulsion; and
    wherein melanin is increased by 15 to 40% in the melanocytes.

* * * * *